US009038514B2

(12) United States Patent
Severino et al.

(10) Patent No.: US 9,038,514 B2
(45) Date of Patent: May 26, 2015

(54) FABRIC CUTTING SYSTEM AND METHOD

(71) Applicant: Atex Technologies, Inc., Pinebluff, NC (US)

(72) Inventors: Danny Severino, Pinehurst, NC (US); Paul Van Hulle, Aberdeen, NC (US); Timothy Warner, Whispering Pines, NC (US)

(73) Assignee: ATEX TECHNOLOGIES, INC., Pinebluff, NC (US)

( * ) Notice: Subject to any disclaimer, the term of this patent is extended or adjusted under 35 U.S.C. 154(b) by 0 days.

(21) Appl. No.: 13/949,331

(22) Filed: Jul. 24, 2013

(65) Prior Publication Data
US 2013/0338432 A1    Dec. 19, 2013

Related U.S. Application Data

(62) Division of application No. 12/836,083, filed on Jul. 14, 2010, now Pat. No. 8,540,619.

(51) Int. Cl.
| | | |
|---|---|---|
| B26D 7/06 | (2006.01) | |
| A61F 2/06 | (2013.01) | |
| B23K 26/40 | (2014.01) | |
| B23K 26/38 | (2014.01) | |

(52) U.S. Cl.
CPC .............. *A61F 2/06* (2013.01); *B23K 26/4055* (2013.01); *B23K 26/38* (2013.01); *Y10S 408/701* (2013.01)

(58) Field of Classification Search
None
See application file for complete search history.

(56) References Cited

U.S. PATENT DOCUMENTS

| | | | | |
|---|---|---|---|---|
| 3,029,819 A * | 4/1962 | Starks | ........................ | 623/1.51 |
| 3,142,067 A * | 7/1964 | Liebig | ......................... | 623/1.51 |
| 5,628,782 A * | 5/1997 | Myers et al. | ................ | 623/2.25 |
| 5,780,807 A * | 7/1998 | Saunders | ................ | 219/121.71 |
| 5,976,650 A * | 11/1999 | Campbell et al. | ............ | 428/35.7 |
| 6,159,565 A * | 12/2000 | Campbell et al. | ............ | 428/35.7 |
| 6,278,079 B1 * | 8/2001 | McIntyre et al. | ........ | 219/121.67 |
| 7,364,587 B2 * | 4/2008 | Dong et al. | ................... | 623/1.5 |
| 7,622,070 B2 * | 11/2009 | Atladottir et al. | ............. | 264/400 |
| 7,682,304 B2 * | 3/2010 | Heyninck-Jantz et al. | ..... | 600/36 |
| 8,066,762 B2 * | 11/2011 | Atladottir et al. | ............ | 623/1.42 |
| 8,242,409 B2 * | 8/2012 | Prabhu | ..................... | 219/121.72 |
| 8,257,431 B2 * | 9/2012 | Henderson et al. | .......... | 623/1.35 |
| 8,540,619 B2 * | 9/2013 | Severino et al. | ................ | 600/36 |
| 8,709,067 B2 * | 4/2014 | Cragg et al. | ................. | 623/1.35 |
| 8,808,352 B2 * | 8/2014 | Eells et al. | .................... | 623/1.13 |
| 2002/0193866 A1 * | 12/2002 | Saunders | ..................... | 623/1.15 |
| 2004/0088037 A1 * | 5/2004 | Nachreiner et al. | ......... | 623/1.15 |
| 2005/0187604 A1 * | 8/2005 | Eells et al. | .................... | 623/1.13 |
| 2006/0058862 A1 * | 3/2006 | Dong et al. | .................... | 623/1.5 |
| 2006/0185142 A1 * | 8/2006 | Nachreiner et al. | ........... | 29/33.5 |
| 2007/0034615 A1 * | 2/2007 | Kleine | ..................... | 219/121.72 |
| 2008/0021540 A1 * | 1/2008 | Saunders | ..................... | 623/1.15 |

(Continued)

Primary Examiner — David E Graybill
(74) Attorney, Agent, or Firm — Hoffman & Baron, LLP

(57) ABSTRACT

A fabric cutting system and/or method can include a mandrel having a body and first and second legs, a centered chuck, and an offset chuck, each chuck configured to receive either one of the legs or body to rotatingly support the mandrel between the chucks. When one of the legs is inserted into the centered chuck and the mandrel body is inserted into the offset chuck, the mandrel can be rotated and the fabric mounted on the mandrel can be cut about the leg at a location beyond the end of the other leg. One of the legs can include a leg extension removable from a leg base that when removed allows the other leg to be cut beyond the end of the leg base. The fabric can be cut with a cutting laser, which may be a multi-axis laser, and/or have low power.

10 Claims, 13 Drawing Sheets

(56) References Cited

U.S. PATENT DOCUMENTS

2008/0103587 A1* 5/2008 Henderson et al. .......... 623/1.35
2010/0100171 A1* 4/2010 Atladottir et al. ............ 623/1.42
2010/0193482 A1* 8/2010 Ow et al. ................. 219/121.67
2010/0256742 A1* 10/2010 Kleine et al. ................. 623/1.16
2011/0056350 A1* 3/2011 Gale et al. ........................ 83/54
2012/0012569 A1* 1/2012 Severino ................. 219/121.72
2012/0013061 A1* 1/2012 Atladottir et al. ................ 269/47
2013/0119586 A1* 5/2013 Gale et al. ..................... 264/400
2013/0123904 A1* 5/2013 Cragg et al. ................. 623/1.16
2013/0338432 A1* 12/2013 Severino et al. ................ 600/36

* cited by examiner

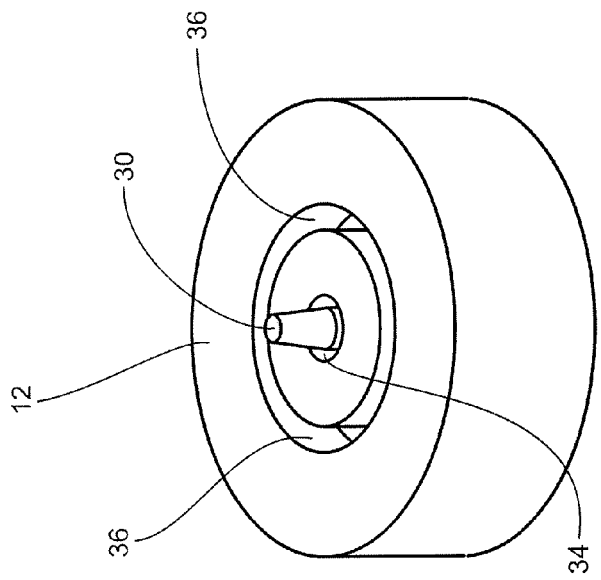
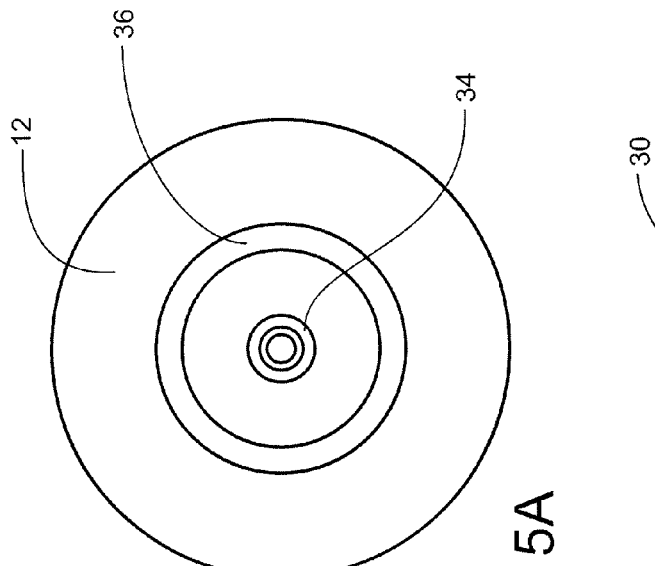
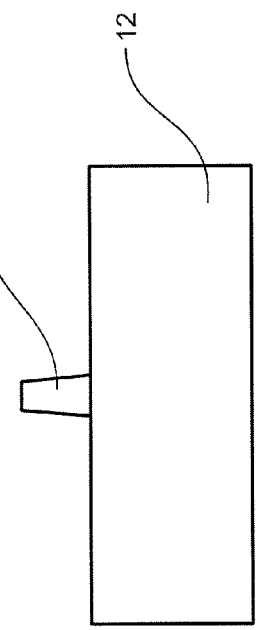
Fig. 5C
Fig 5A
Fig. 5B

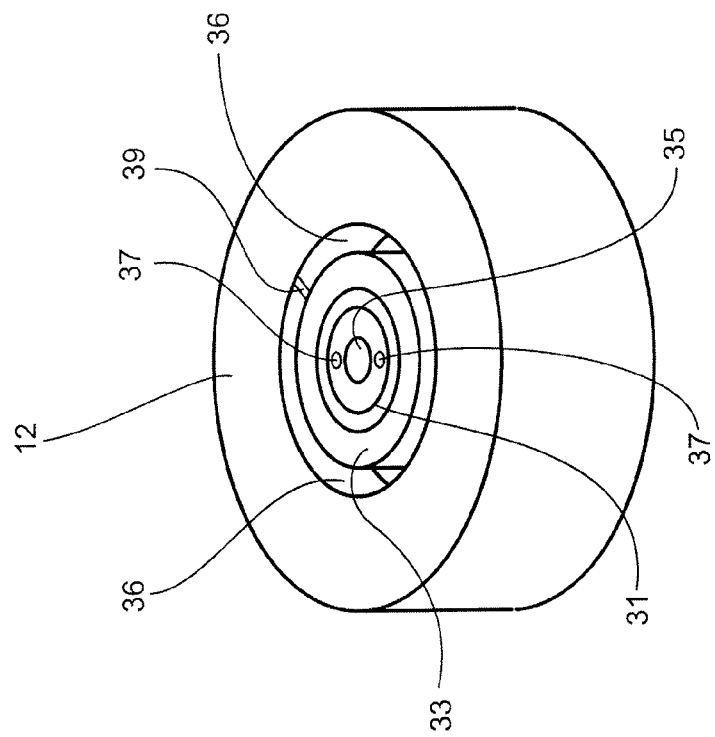
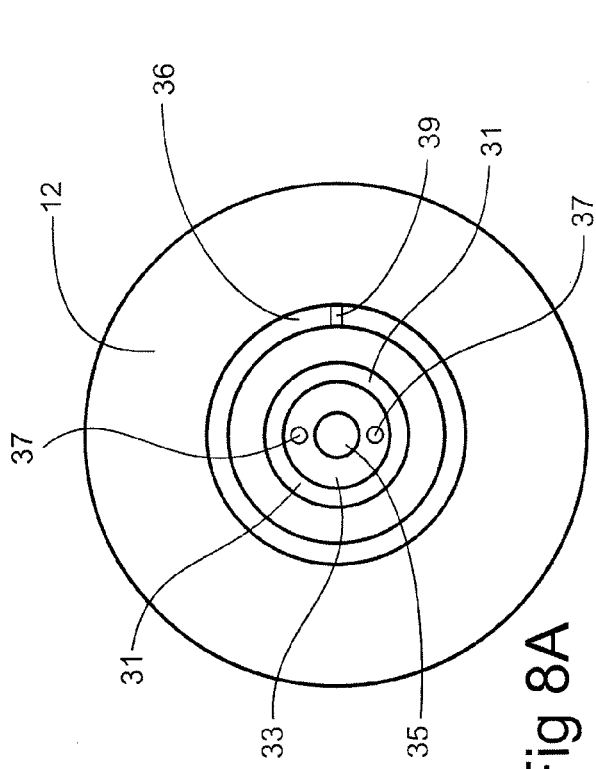
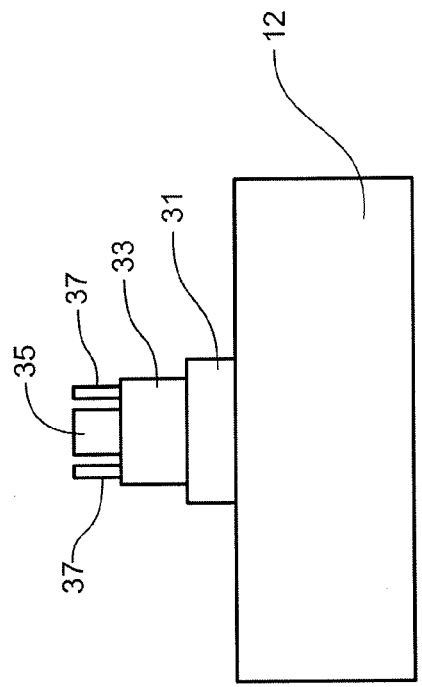

FABRIC CUTTING SYSTEM AND METHOD

FIELD OF THE INVENTION

The present invention relates to a fabric cutting system and method. Embodiments of the present invention are advantageous for providing tubular fabrics having evenly cut and sealed edges.

BACKGROUND OF THE INVENTION

Tubular fabrics intended for use in medical applications often have complex shapes and are usually cut by hand. A conventional technique for cutting fabric for use in medical applications includes manually heat-cutting the fabric with a soldering iron-type tool. Manual heat-cutting often results in an uneven edge and loose fibers extending from the cut line. In some processes, such heat-cutting is followed by manually trimming the cut edge with scissors under a microscope in attempt to correct uneven areas and decrease the number of loose fibers. However, because the second, trimming step is also a manual step, unevenly cut fibers from the original heat cut and/or the scissors cut can remain along the cut edge, creating a risk for fraying. Another disadvantage of such a manual cutting process is that the second cut with scissors represents "re-work" designed to correct imprecision in the first cut. Thus, a second, labor-intensive cutting step increases the cost of the manufacturing process.

In tubular fabrics, for example, fabrics for use as an endovascular graft, the fabric is manually rotated to cut the fabric around the circumference of the tube. A disadvantage of manually rotating and cutting the tubular fabric is that moving the fabric from one position to another can further cause imprecise or even cuts. In addition, manual cutting can lead to variability in quality of cuts between different operators.

After the fabric is cut twice—first by a soldering iron-type tool and then by trimming with scissors—the fabric edge can be placed under a microscope and "lightly" heat sealed so as not to further disturb the trimmed edge. However, a disadvantage of "light" heat sealing is that routine handling of the fabric can disrupt the "light" seal, thereby allowing cut yarn ends to become loose and possibly cause the fabric to fray and/or unravel.

Some tubular fabrics can have two or more adjacent tubular extents, for example, an endovascular graft that has bifurcated legs for placement into two smaller arteries branching from a larger artery. Such adjacent-leg tubular fabrics create another cutting challenge. A tubular fabric having two adjacent legs can be mounted on a mandrel for rotating while a cut is being made about the circumference of the legs. However, when the tubular fabric is rotated, a cutting tool cannot reach the "inside" portions of the legs that are facing each other. In some conventional cutting techniques, the legs of the mandrel are loosened from the mandrel body, rotated, and re-tightened so as to exposed the uncut portions for cutting. This movement of the mandrel legs can cause movement of the fabric about the legs. As a result, such movement in conventional cutting techniques can cause unevenness between the two partial cuts on each leg, and undesirably allows one leg to be cut a different length than the other leg.

The tolerance for cuts of fabrics used in many medical devices is narrow, for example, less than about 0.5 mm from the intended line of cut. Therefore, quality control variances in manually rotated and cut fabrics and in fabrics having adjacent tubes that are partially cut, repositioned, and finish cut are often unacceptable in fabrics designed for use in medical applications, particularly in implantable medical devices.

Thus, there is a need to provide a fabric cutting system and method that provide reliably precise cuts. There is also a need for such a fabric cutting system and method that meet quality control requirements for tubular fabrics used in medical applications. There is also a need for such a fabric cutting system and method that provides a completely sealed edge at a cut location. There is also a need for such a fabric cutting system and method that are efficient and cost-effective.

SUMMARY OF THE INVENTION

The present invention provides a fabric cutting system and method. In an illustrative embodiment, a fabric cutting system can comprise a mandrel, a centered chuck, an offset chuck, and a fabric cutting tool. The mandrel can be configured to support a tubular fabric having a plurality of fabric legs, and comprise a body, a first leg, and a second leg shorter than the first leg. The centered chuck can be fixedly attached to a work surface and configured to receive either one of the mandrel legs or the body to rotatingly support the mandrel in the center of the centered chuck. The offset chuck can be spaced apart from and opposed to the centered chuck, movably attached to the work surface, and configured to receive either one of the mandrel legs or the body to rotatingly support the mandrel at a point offset from the center of the offset chuck. When the first leg is inserted into the centered chuck and the mandrel body is inserted into the offset chuck, the mandrel can be rotated and the fabric mounted on the mandrel can be cut about the first leg at a location beyond the end of the second leg.

In some embodiments, the first leg can further comprise a leg base and a leg extension removably attachable to the leg base. When the leg extension is removed from the leg base, the second leg is inserted into the centered chuck, and the mandrel body is inserted into the offset chuck, the mandrel can be rotated and the fabric can be cut about the second leg at a location beyond the end of the first leg. In some embodiments, when the mandrel body is inserted into the centered chuck and the second leg is inserted into the offset chuck, the mandrel can be rotated and the fabric can be cut about the mandrel body. In each of these embodiments, the fabric on the mandrel can be cut by the cutting tool having a line of contact with the particular location unimpeded by the other leg. In certain embodiments, the fabric cut on the mandrel comprises a vascular graft.

In some embodiments, the fabric cutting tool can comprise a cutting laser. The cutting laser can have the capability to be programmed with different focal distances for cutting different diameters on the mandrel. In certain embodiments, the cutting laser can comprise a multi-axis laser having a plurality of power heads, each power head adapted to emit a laser beam to a different focal cutting point. In certain embodiments, the cutting laser can emit a laser beam having between about 30 and about 35 watts of power to cut the fabric.

Some embodiments of the present invention can include a method of cutting a fabric utilizing the fabric cutting system described herein.

Features of a fabric cutting system and method of the present invention may be accomplished singularly, or in combination, in one or more of the embodiments of the present invention. As will be realized by those of skill in the art, many different embodiments of a fabric cutting system and method according to the present invention are possible. Additional uses, advantages, and features of the invention are set forth in the illustrative embodiments discussed in the detailed description herein and will become more apparent to those skilled in the art upon examination of the following.

BRIEF DESCRIPTION OF THE DRAWINGS

FIG. 5A is a diagrammatic top view of the centered chuck shown in FIG. 1.

FIG. 5B is a diagrammatic side view of the centered chuck shown in FIG. 1.

FIG. 5C is a diagrammatic perspective view of the centered chuck shown in FIG. 1.

FIG. 8A is a diagrammatic top view of the centered chuck shown in FIG. 7.

FIG. 8B is a diagrammatic side view of the centered chuck shown in FIG. 7.

FIG. 8C is a diagrammatic perspective view of the centered chuck shown in FIG. 7.

DETAILED DESCRIPTION

Figure 1:
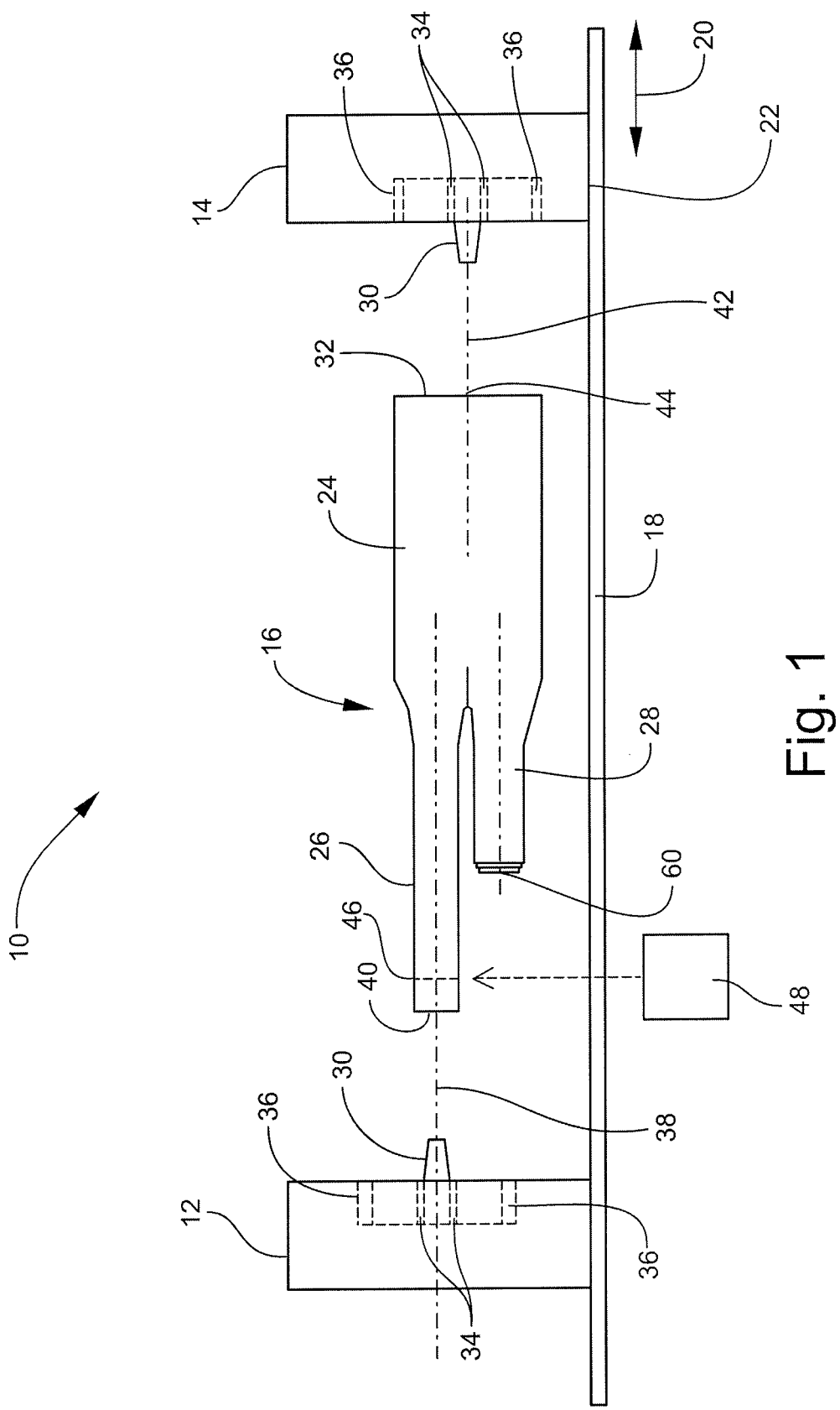
FIG. 1 is a diagrammatic side view of a fabric cutting system comprising a mandrel, a centered chuck, and an offset chuck in an embodiment of the present invention.

For the purposes of this specification, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the embodiments described herein. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the described embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, for example, 5.5 to 10.

For the purposes of this specification, terms such as "forward," "rearward," "front," "back," "right," "left," "upwardly," "downwardly," and the like are words of convenience and are not to be construed as limiting terms. As used in this specification and the appended claims, the singular forms "a," "an," and "the" include plural referents unless the context clearly dictates otherwise. Thus, for example, the term "a leg" is intended to mean a single leg or more than one leg. In addition, any reference referred to as being "incorporated herein" is to be understood as being incorporated in its entirety.

The present invention can include embodiments of a fabric cutting system. Such a system can be utilized to provide tubular fabrics having more than one leg, or lumen, in which the fabric has quality-cut and well-sealed edges that resist fraying. As shown in the illustrative embodiment in FIGS. 1-6 and 11, the fabric cutting system 10 can comprise two chucks 12, 14 and a mandrel 16. For purposes herein, "chuck" is defined as a device that holds a tool or the material being worked on in a machine or to a work surface. For purposes herein, "mandrel" is defined as a rod-like structure about which material can be shaped. For example, the mandrel 16 can be a cylindrically-shaped, or tubular-shaped, metal structure about which a fabric can be shaped to a form suitable for a tubular implantable medical application, such as a vascular graft.

In the embodiment shown in FIGS. 1-6, the two chucks 12, 14 include a first, centered chuck 12 that is fixedly attached to a work surface 18, and a second, offset chuck 14 that is spaced apart from the centered chuck 12 and movably attached to the work surface 18. The offset chuck 14 can be moved on the work surface 18 along a direction of movement 20 toward and away from the centered chuck 12. The offset chuck 14 can be moved toward the centered chuck 12 and clamped with a clamping mechanism 22 into a position on the work surface 18 so as to secure the mandrel 16 between the two chucks 12, 14 for working on fabric on the mandrel 16. The offset chuck 14 can be moved away from the centered chuck 12 to release the mandrel 16 from the two chucks 12, 14.

The mandrel 16 can include a body 24 and at least one limb, or leg, having a lumen and extending from the mandrel body 24. In the embodiment shown in FIGS. 1-4, the mandrel 16 can include a first, longer leg 26 and a second, shorter leg 28. Such a mandrel leg configuration can be utilized for forming a fabric having a longer leg and a shorter leg useful, for example, in a vascular graft implantable into an artery and two unaligned or uneven arterial branches.

The mandrel 16 can be rotatably positioned between the two spaced-apart chucks 12, 14. Each of the chucks 12, 14 can be substantially the same size as the other, and the center of each chuck 12, 14 can be the same vertical distance from the work surface 18. In the embodiment in FIGS. 1-4 and 11, each of the centered and offset chucks 12, 14, respectively, includes a tapered mount 30 extending outwardly from the respective chuck 12, 14 toward the other chuck 12, 14. In the centered chuck 12, the tapered mount 30 extends outwardly from the center of the chuck 12, as shown in FIGS. 1-4, 5A, 5B, 5C, and 11. In the offset chuck 14, the tapered mount 30 extends outwardly from a position offset below the center of the chuck 14 closer to the work surface 18 than the tapered mount 30 in the centered chuck 12, as shown in FIGS. 1-4, 6A, 6B, and 11. The offset of the tapered mount 30 from the center of the offset chuck 12 allows the larger diameter body 24 and the smaller diameter legs 26, 28 of the mandrel 16 to rotate together. The tapered mounts 30 can have the same configuration (such as same size and shape) so that each tapered mount 30 can be inserted into either of the ends of the larger base 32 of the mandrel body 24 and/or one of the legs 26, 28 of the mandrel 16. The ends of the mandrel base 32 and the legs 26, 28 can be configured to receive the tapered mounts 30, for example, in a configuration mated to the size and shape of the tapered mounts 30.

Figure 6A:
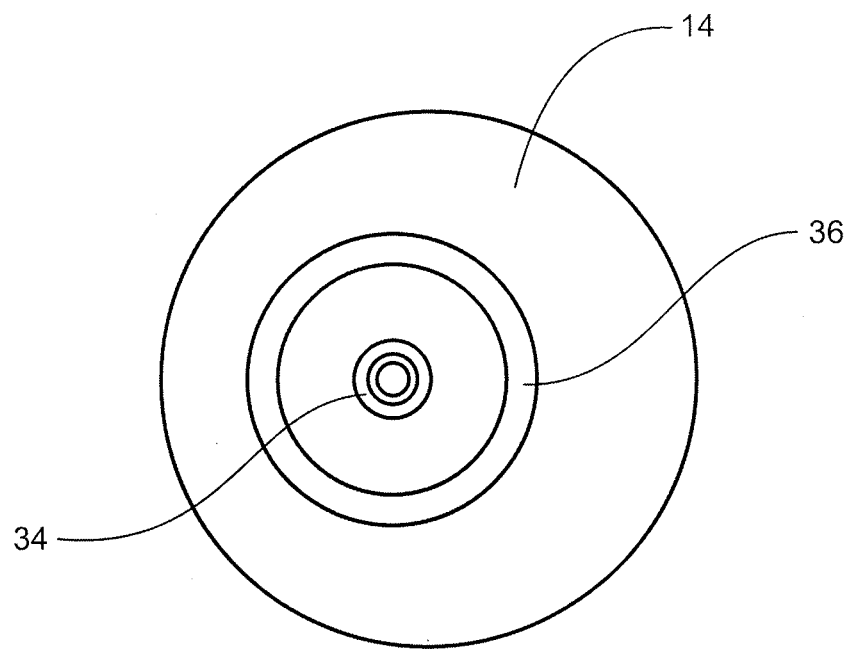
FIG. 6A is a diagrammatic top view of the offset chuck shown in FIG. 1.
Figure 6B:
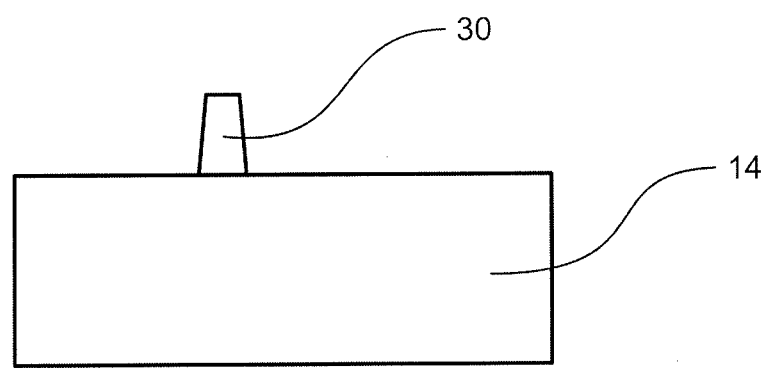
FIG. 6B is a diagrammatic side view of the offset chuck shown in FIG. 1.

Each of the chucks 12, 14 can include at least two concentric grooves 34, 36 formed in the face of the chucks 12, 14, as shown in the embodiment in FIGS. 1-4, and more particularly in FIGS. 5A, 5C, and 6A. Each of the grooves 34, 36 is centered about the tapered mount 30 extending outwardly from the chuck 12, 14. In some embodiments, the mandrel 16 can be hollow or partially hollow. Preferably, at least the ends of the first and second legs 26, 28, respectively, and the base 32 of the mandrel 16 are hollow so that the ends of the legs 26, 28 and the mandrel base 32 can be inserted into the grooves 34, 36 in the chucks 12, 14. One of the grooves is an inner, leg groove 34 encircling the base of the tapered mount 30. The leg groove 34 is sized to allow the ends of the first and second legs 26, 28, respectively, to be inserted into the leg groove 34 about the tapered mount 30. Another groove is an outer, body groove 36 having a circumference larger than that of the leg groove 34. The body groove 36 is sized to allow the end of the base 32 of the mandrel body 24 to be inserted into the body groove 36. The ends of the legs 26, 28 and the mandrel body 24 can be press fit into the leg groove 34 and body groove 36, respectively, and held in place in the chucks 12, 14 by pressure from the chucks 12, 14 on the mandrel 16 when the offset chuck 14 is clamped into position on the work surface 18. In this manner, when the mandrel 16 is positioned between the chucks 12, 14, the mandrel 16 is supported within the leg and body grooves 34, 36, respectively, for rotation with and/or by the chucks 12, 14.

In some embodiments, the centered and offset chucks 12, 14, respectively, can each include more than one leg groove 34. For example, each chuck 12, 14 can include two leg grooves 34, each having a different circumference so as to accommodate mandrel legs having different diameters.

Figure 7:
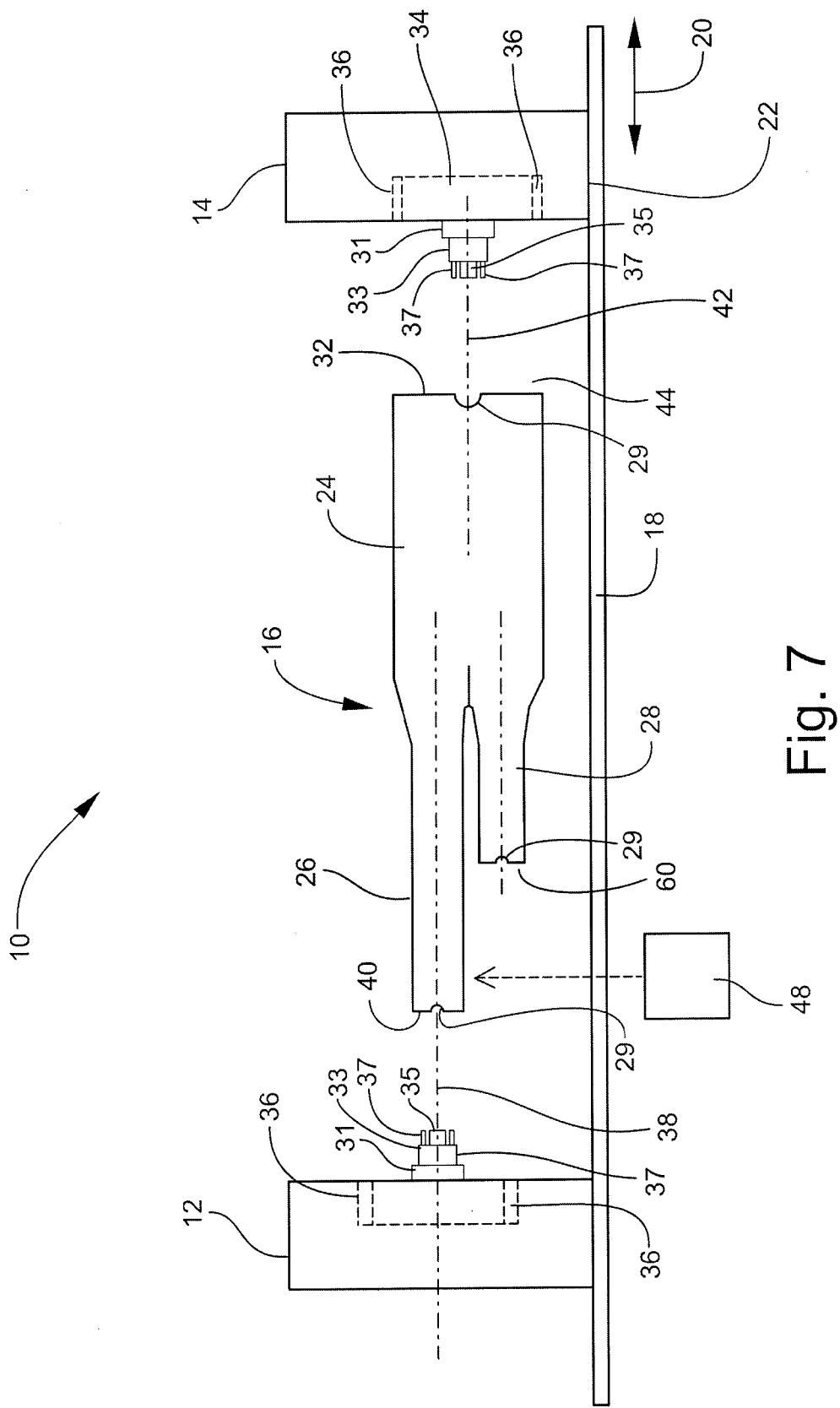
FIG. 7 is a diagrammatic side view of a fabric cutting system comprising a mandrel, a centered chuck, and an offset chuck in another embodiment of the present invention.

In another embodiment, as shown in FIG. 7, each of the centered and offset chucks 12, 14, respectively, includes a stepped mount having a first stepped portion 31, a second stepped portion 33, and a third stepped portion 35. The first portion 31 has a diameter that fits within the circumference, and extends outwardly from the center of, the body groove 36 in the respective chuck 12, 14 toward the other chuck 12, 14. The second portion 33 has a diameter smaller than the diameter of the first stepped portion 31, and extends outwardly from the center of the first portion 31. The third stepped portion 35 has a diameter smaller than the diameter of the second stepped portion 33, and extends outwardly from the center of the second portion 33. A pair of rounded leg pins 37 extend outwardly from the second stepped portion 33 adjacent the third stepped portion 35. The leg pins 37 can be on opposite sides of the third stepped portion 35. The leg pins 37 can be any suitable material, such as the material comprising the chuck 12, 14, for example, a polymeric material, or a metallic material such as stainless steel.

Figure 9A:
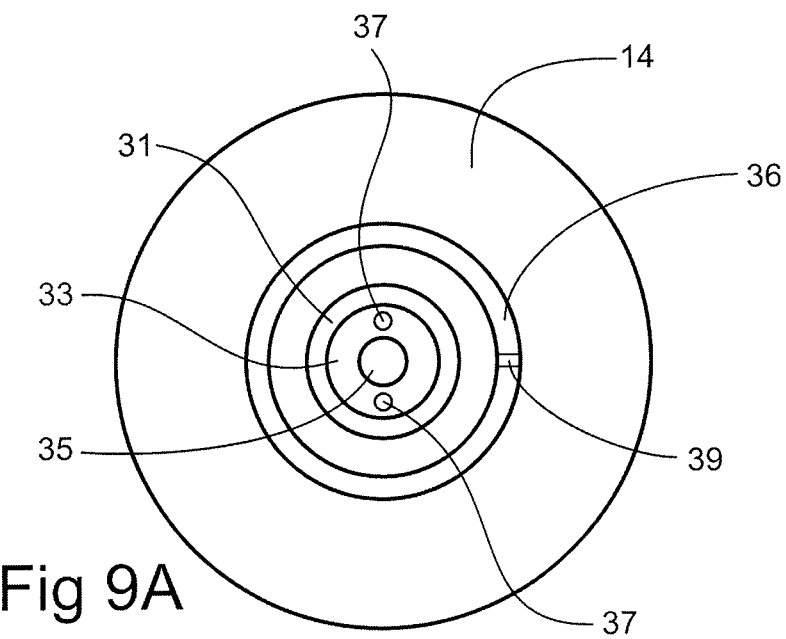
FIG. 9A is a diagrammatic top view of the offset chuck shown in FIG. 7.
Figure 9B:
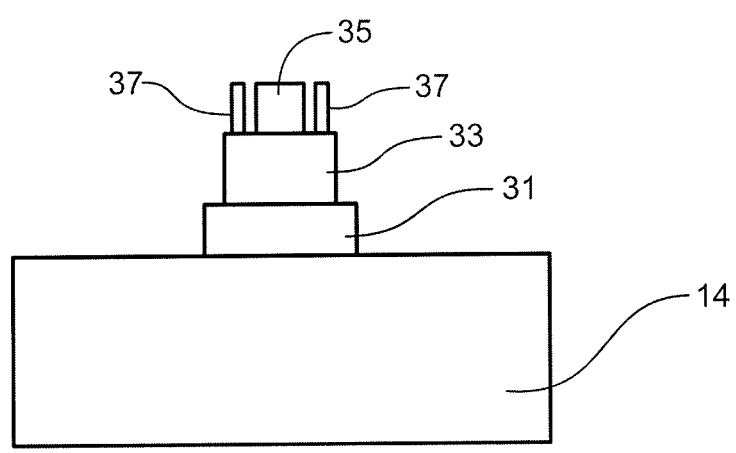
FIG. 9B is a diagrammatic side view of the offset chuck shown in FIG. 7.

In the centered chuck 12, the stepped mount portions 31, 33, 35 extend outwardly from the center of the chuck 12, as shown in FIGS. 7, 8A, 8B, and 8C. In the offset chuck 14, the stepped mount portions 31, 33, 35 extend outwardly from a position offset below the center of the chuck 14 closer to the work surface 18 than the stepped mount portions 31, 33, 35 in the centered chuck 12, as shown in FIGS. 7, 9A, and 9B. The offset of the stepped mount portions 31, 33, 35 from the center of the offset chuck 12 allows the larger body 24 and the smaller legs 26, 28 of the mandrel 16 to rotate together. The stepped mount portions 31, 33, 35 can each have the same configuration (such as same size and shape) so that each stepped mount can be inserted into the end of either of the legs 26, 28 of the mandrel 16 or the mandrel body 24. The ends of the legs 26, 28 can be configured to engagingly fit about the third stepped portion 35 and leg pins 37, for example, in a configuration mated to the size and shape of the third stepped portion 35 and leg pins 37. For example, as shown in FIG. 7, the ends of the legs 26, 28 can each include a pair of opposed notches 29. The notches 29 can be configured so as to slide over and engage the leg pins 37 about the stepped mount third portion 35. When the notches 29 in one of the mandrel legs 26, 28 engages the leg pins 37, the mandrel 16 can be rotated with the chuck 12, 14.

As shown in the embodiment in FIGS. 7, 8A, 8C, and 9A, each of the chucks 12, 14 includes the body groove 36 formed in the face of the chucks 12, 14. The body groove 36 is centered about the stepped mount portions 31, 33, 35. At least the end of the mandrel base 32 is hollow so that the end of the mandrel base 32 can be inserted over the stepped mount portions 31, 33, 35 and into the body groove 36 in the chucks 12, 14. The end the mandrel body 24 can be press fit into the body groove 36 and held in place in the chucks 12, 14 by pressure from the chucks 12, 14 on the mandrel 16 when the offset chuck 14 is clamped into position on the work surface 18. In this manner, when the mandrel 16 is positioned between the chucks 12, 14, one of the mandrel legs 26, 28 is supported by the stepped mount portions 31, 33, 35 extending from one of the chucks 12, 14 and the mandrel body 24 is supported by the body groove 36 in the other chuck 12, 14 for rotation with and/or by the chucks 12, 14.

As shown in FIGS. 8A, 8C, and 9A, at least one base pin 39 can extend between the inner and outer diameters of the body groove 36 in the chucks 12, 14. The base pin 39 can be any suitable material, such as the material comprising the chuck 12, 14, for example, a polymeric material, or a metallic material such as stainless steel. As shown in FIG. 7, the end of the mandrel base 32 can include a pair of opposed notches 29. The notches 29 can be configured so that one of the notches 29 can to slide over and engage the base pin 39 in the body groove 36. When one of the notches 29 in the mandrel base 32 engages the base pin 39, the mandrel 16 can be rotated with the chuck 12, 14. In some embodiments, the chucks 12, 14 shown in FIG. 1-6 can also include at least one base pin 39 extending between the inner and outer diameters of the body groove 36 for engaging the notch 29 in the mandrel base 32.

Figure 10A:
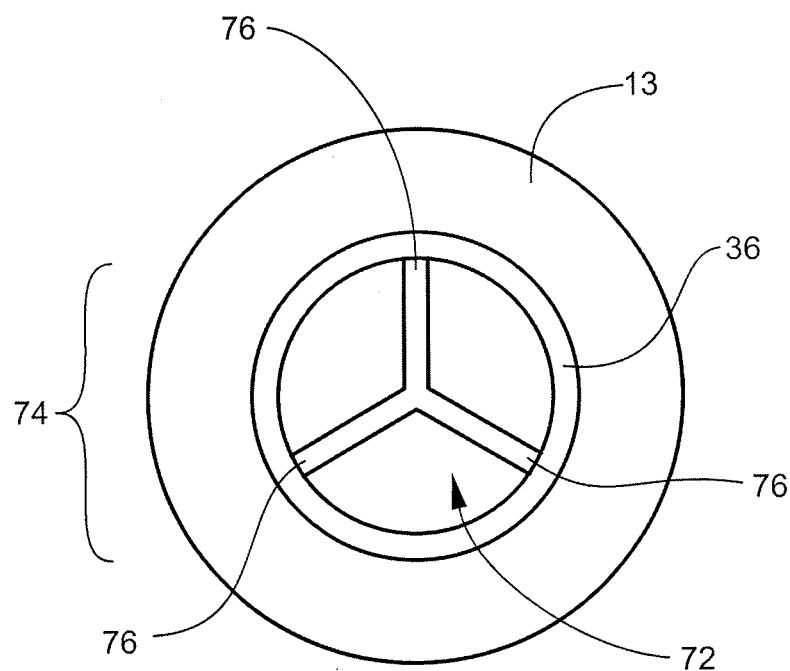
FIG. 10A is a diagrammatic top view of a centered chuck in another embodiment of the present invention.
Figure 10B:
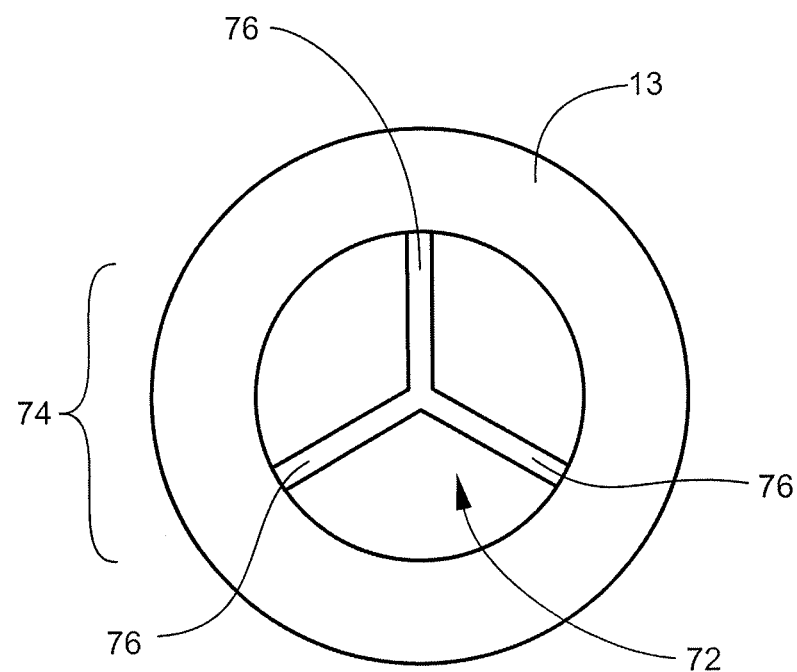
FIG. 10B is a diagrammatic top view of a centered chuck in another embodiment of the present invention.

In another embodiment, as shown in FIGS. 10A and 10B, an alternative centered chuck 13 can include a universal leg engaging member 72 having a "Y" shape. The universal leg engaging member 72 can extend outwardly from the chuck, for example, about ⅛ inch to about ¼ inch. The universal leg engaging member 72 can comprise various materials, such as the material comprising the chuck 12, 14, for example, a polymeric material, or a metallic material such as stainless steel. The universal leg engaging member 72 can be secured to the face of the chuck 13 in various ways. In a preferred embodiment, the chuck 13 includes a Y-shaped groove (not shown) in the face of the chuck corresponding to the shape and dimensions of the leg engaging member 72. A stainless steel leg engaging member 72 is inserted into and fixedly attached to the groove such that the leg engaging member 72 is secured to and extends upwardly from the chuck 13.

The ends of the mandrel legs 26, 28 can be configured to engagingly fit onto the universal leg engaging member 72. For example, the ends of the legs 26, 28 can each include three notches 29 equally spaced about the circumference of the ends of the legs 26, 28 (that is, spaced 120 degrees apart). The notches 29 can be configured so as to slide over and engage the universal leg engaging member 72. When the notches 29 in one of the mandrel legs 26, 28 engages the universal leg engaging member 72, the mandrel 16 can be rotated with the chucks 13, 14.

Each of the arms 76 of the Y-shaped universal leg engaging member 72 extend outwardly from the center of the chuck 13 toward the edge of the face of the chuck 13. In this configuration, a mandrel leg 26, 28 having a first, smaller diameter can fit about the leg engaging member 72 at a point relatively close to the center of the chuck 13, while a mandrel leg 26, 28 having a second, larger diameter can fit about the leg engaging member 72 farther from the center of the chuck 13 than the smaller diameter leg 26, 28. Thus, mandrel legs 26, 28 having different diameters can fit about the leg engaging member 72. In this way, some embodiments of the fabric cutting system 10 including the chuck 13 can accommodate mandrel legs 26, 28 having different diameters without having to change the chuck 13.

In some embodiments the centered chuck 13 can include the body groove 36, as shown in FIG. 10A. The centered chuck 13 having the universal leg engaging member 72 does not include the leg groove 34. In this embodiment, the universal leg engaging member 72 can extend in a "Y" shape from the center of the chuck 13 toward, and/or the entire distance to, the inside diameter of the body groove 36. In other embodiments, the centered chuck 13 does not include the body groove 36, as shown in FIG. 10B. In such an embodiment, the universal leg engaging member 72 can extend in a "Y" shape from the center of the chuck 13 toward, and/or the entire distance to, the outer circumferential perimeter of the chuck 13. Accordingly, the centered chuck 13 having the universal leg engaging member 72 can accommodate mandrel legs 26, 28 having a diameter equivalent to the diameter 74 of a circle circumscribing the universal leg engaging member 72.

The centered chuck 13 having the universal leg engaging member 72 can be utilized in conjunction with the offset chuck 14 having the body groove 36, as shown in FIGS. 1-6 and 11, to support a mandrel between the chucks 13, 14 for rotation. Alternatively, the offset chuck 14 can also include the universal leg engaging member 72 extending outwardly from a position offset from the center of the chuck 14. Thus, when utilized with the centered chuck 13 having the body groove 36, as shown in FIG. 10A, an appropriately configured mandrel can be supported on either end by either the centered chuck 13 or the offset chuck 14 having the universal leg engaging member 72.

In an embodiment comprising at least the chuck 13 having the body groove 36, at least the end of the mandrel base 32 is hollow so that the end of the mandrel base 32 can be inserted over the universal leg engaging member 72 and into the body groove 36 in the chuck 13. The end the mandrel body 24 can be press fit into the body groove 36 and held in place in the chucks 13, 14 by pressure from the chucks 13, 14 on the mandrel 16 when the offset chuck 14 is clamped into position on the work surface 18. In this manner, when the mandrel 16 is positioned between the chucks 13, 14, one of the mandrel legs 26, 28 is supported by the universal leg engaging member 72 extending from one of the chucks 13, 14 and the mandrel body 24 is supported by the body groove 36 in the other chuck 13, 14 for rotation with and/or by the chucks 13, 14.

After a fabric is mounted onto the mandrel 16 and the mandrel 16 is positioned between the centered and offset chucks 12, 14, respectively, the fabric can be cut at desired locations. The fabric can be any fabric suitable for cutting on a mandrel. In certain embodiments, the fabric can be fabric suitable for forming implantable tubular medical devices. For example, in particular applications, the fabric can comprise polypropylene and/or polyester.

In operation, the first, longer leg 26 of the mandrel 16 is aligned and engaged with the centered chuck 12 along a first longitudinal axis 38 through the center of the centered chuck 12 and the center 40 of the first leg 26. In some embodiments, as in FIGS. 1-6 and 11, the end of the first leg 26 is inserted into the leg groove 34 in the centered chuck 12. In other embodiments, as in FIGS. 7-9, the notches 29 in the end of the first leg 26 are slid over and engage the leg pins 37 about the stepped mount third portion 35. In still other embodiments, as in FIG. 10, the notches 29 in the ends of the first leg 26 are mounted onto and engage the universal leg engaging member 72. The base 32 of the mandrel 16 is aligned and engaged with the offset chuck 14 along a second longitudinal axis 42 through the center of the offset chuck and the center 44 of the base 32 of the mandrel body 24. The end of the mandrel base 32 is inserted into the body groove 36 in the offset chuck 14. The offset chuck 14 is then moved toward the centered chuck 12 such that the mandrel 16 is supported on each end by one of the chucks 12, 14 for rotation. Once the fabric cutting system 10 assembly is in place for rotating the mandrel 16, the offset chuck 14 is clamped to the work surface 18 with the clamping mechanism 22 to secure the assembly in place for operation.

Then, a fabric mounted onto the mandrel 16 can be cut about the first leg 26. The first leg cut 46 can be located on the first leg 26 beyond the end of the second leg 28 toward the centered chuck 12. The mandrel 16 can be rotated about the first and second longitudinal axes 38, 42, respectively, in order to complete the cut 46 about the entire circumference of the first leg 26. In this way, the fabric cutting system 10 provides a direct and unimpeded line of contact between a fabric cutting tool 48 and the first leg 26. That is, the first leg cut 46 can be made while rotating the mandrel 16 without interference from the second leg 28 between the fabric cutting tool 48 and the first leg 26.

To make a cut in fabric on the second, shorter leg 28, the mandrel 16 is first removed from the chucks 12, 14. The clamping mechanism 22 securing the offset chuck 14 to the work surface 18 can be released, and the offset chuck 14 moved away from the centered chuck 12 along the direction of movement 20 on the work surface 18. When the two chucks 12, 14 are thusly separated, the mandrel 16 can be removed from the chucks 12, 14.

Figure 2:
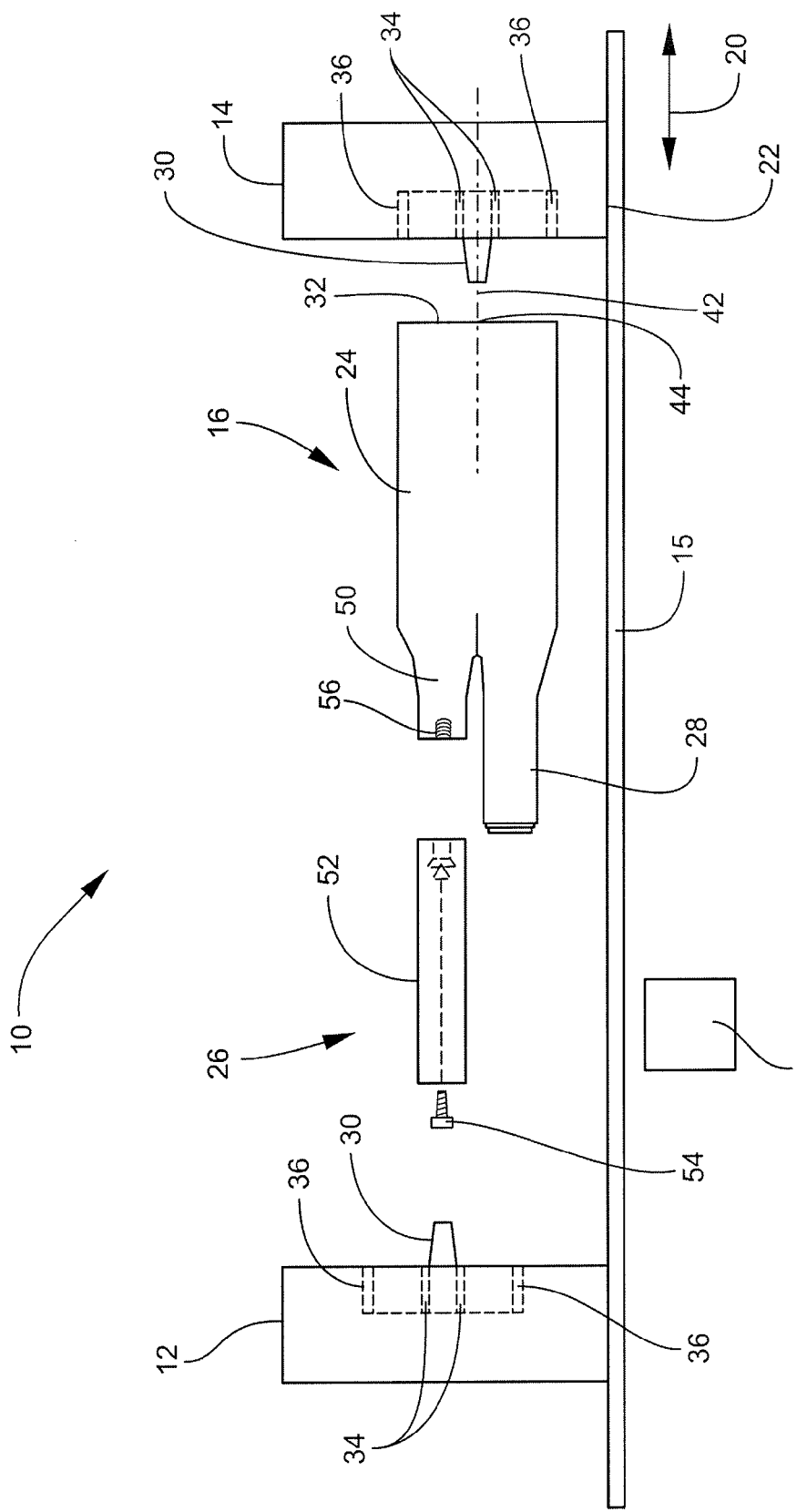
FIG. 2 is a diagrammatic side view of the fabric cutting system shown in FIG. 1, in which the leg extension of one leg of the mandrel is separated from the base of the leg in an embodiment of the present invention.
Figure 3:
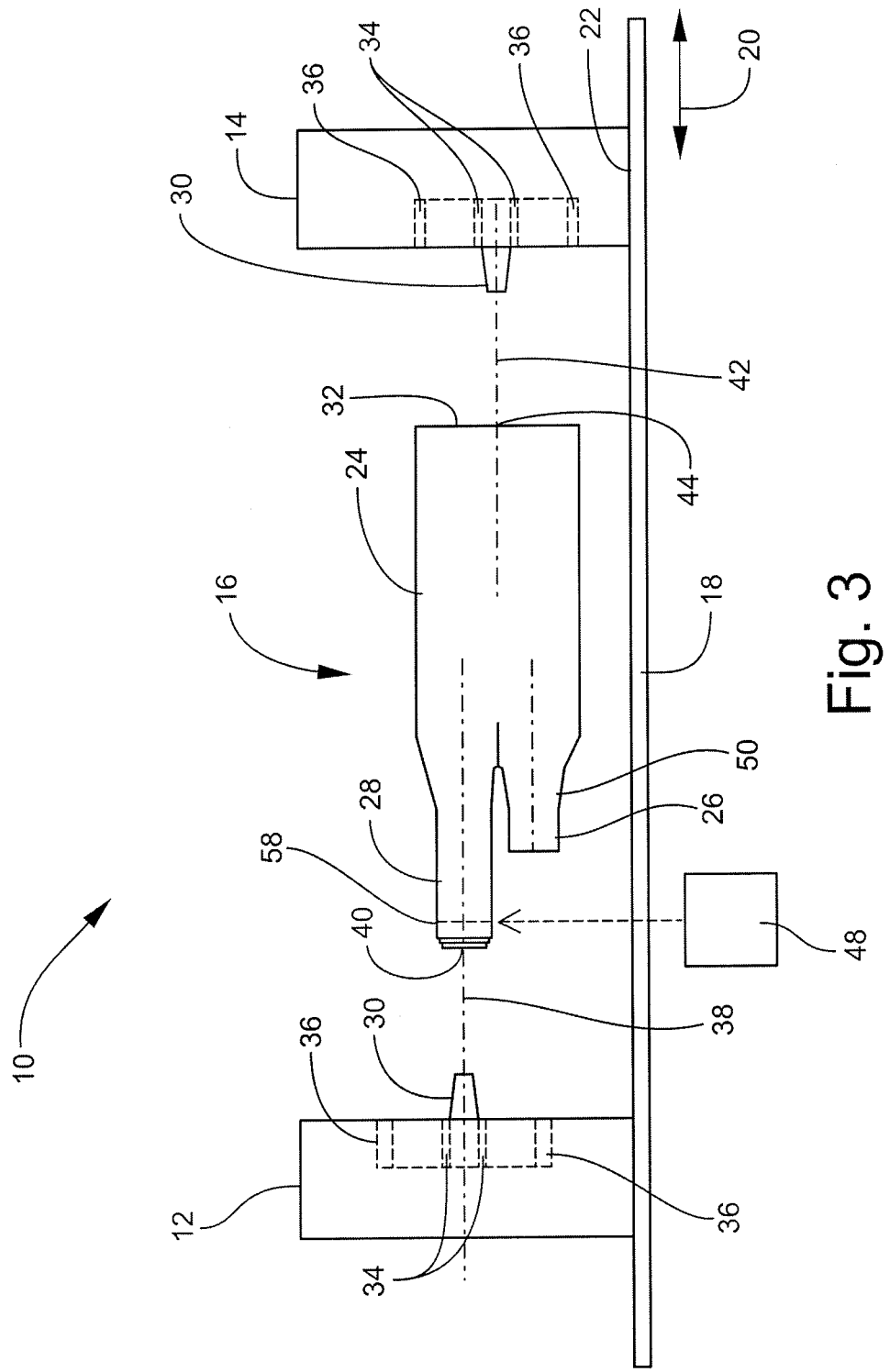
FIG. 3 is a diagrammatic side view of the fabric cutting system shown in FIGS. 1 and 2, in which the positions of the mandrel legs relative to the centered chuck are reversed in an embodiment of the present invention.

In some embodiments, the first, longer leg 26 can comprise a leg base 50 and a leg extension 52 separable from the leg base 50, as shown in FIG. 2. In other embodiments, each of the legs 26, 28 on the mandrel 16 can include a leg base 50 and a separable leg extension 52 such that leg extensions 52 of various lengths can be utilized with either of the leg bases 50.

The leg extension 52 can be removably attached to the leg base 50 in various ways. Preferably, the leg extension 52 can be attached to and removed from the leg base 50 with a quick release mechanism. In one illustrative embodiment of such a quick release mechanism, the leg extension 52 can have a hollow bore sufficiently large to receive a threaded screw 54 through the bore. The leg base 50 can include screw receiving threads 56 inside the leg base 50. When the leg extension 52 and the leg base 50 are abutted together end-to-end, the screw 54 can be inserted through the leg extension bore and threaded into the screw receiving threads 56 in the leg base 50 to secure the leg extension 52 to the leg base 50. For example, the screw 54 can have a hexagonal socket in the head of the screw 54, and a hex key, or Allen wrench, can be inserted through the bore of the leg extension 52 to tighten the screw 54 into the leg base 50 and loosen the screw 54 from the leg base 50. In this way, the leg extension 52 can be quickly and easily secured to and removed from the leg base 50.

In other embodiments, the quick release mechanism can comprise other means of securing the leg extension 52 to the leg base 50. As one example, one of the ends of the leg extension 52 or the leg base 50 can have a "male" configuration insertable into a "female" configuration at the end of the other of the leg extension 52 or leg base 50. When the ends of the leg extension 52 and leg base 50 are joined together, pressure from the two chucks 12, 14 on the mandrel 16 can hold the leg extension 52 and leg base 50 together during operation of the fabric cutting system 10. When the mandrel 16 is removed from the chucks 12, 14, the leg extension 52 can be manually removed from the leg base 50.

After the leg extension 52 is removed from the leg base 50 of the first leg 26, as shown in FIG. 2, the portion of the fabric leg (not shown) extending beyond the leg base 50 can be turned back onto itself to move that fabric leg out of the way for cutting the fabric on the second leg 28. Optionally, an O-ring may be placed about the folded back fabric leg to secure the folded portion about the leg base 50.

Once the mandrel 16 is removed from the chucks 12, 14 and the leg extension 52 removed from the leg base 50, the second leg 28 (which is now the longer of the two legs 26, 28) can be aligned and engaged with the centered chuck 12 along the first longitudinal axis 38 through the center of the centered chuck 12 and the center 60 of the second leg 28. In some embodiments, as in FIGS. 1-6, the end of the second leg 28 is inserted into the leg groove 34 in the centered chuck 12. In other embodiments, as in FIGS. 7-9, the notches 29 in the end of the second leg 28 are slid over and engage the leg pins 37 about the stepped mount third portion 35. In still other embodiments, as in FIG. 10, the notches 29 in the ends of the second leg 28 are mounted onto and engage the universal leg engaging member 72.

As the second leg 28 is aligned and engaged with the centered chuck 12, the base 32 of the mandrel 16 is aligned and engaged with the offset chuck 14 along the second longitudinal axis 42 through the center of the offset chuck 14 and the center 44 of the base 32 of the mandrel body 24. The end of the mandrel base 32 is inserted into the body groove 36 in the offset chuck 14. The offset chuck 14 is then moved toward the centered chuck 12 such that the mandrel 16 is supported on each end by one of the chucks 12, 14 for rotation. When the fabric cutting system 10 assembly is in place for rotating the mandrel 16, the offset chuck 14 is clamped to the work surface 18 with the clamping mechanism 22 to secure the assembly in place for operation. If the second leg 28 has a different diameter than the first leg 26, the fabric cutting tool 48 can be adjusted to accommodate for the difference in diameter.

Then, the fabric mounted onto the mandrel 16 can be cut about the second leg 28. The second leg cut 58 can be located on the second leg 28 beyond the end of the leg base 50 of the first leg 26 toward the centered chuck 12. The mandrel 16 can be rotated about the first and second longitudinal axes 38, 42, respectively, in order to complete the cut 58 about the entire circumference of the second leg 28. In this way, the fabric cutting system 10 provides a direct and unimpeded line of contact between the fabric cutting tool 48 and the second leg 28. That is, the second leg cut 58 can be made while rotating the mandrel 16 without interference from the first leg 26 between the fabric cutting tool 48 and the second leg 28.

Figure 4:
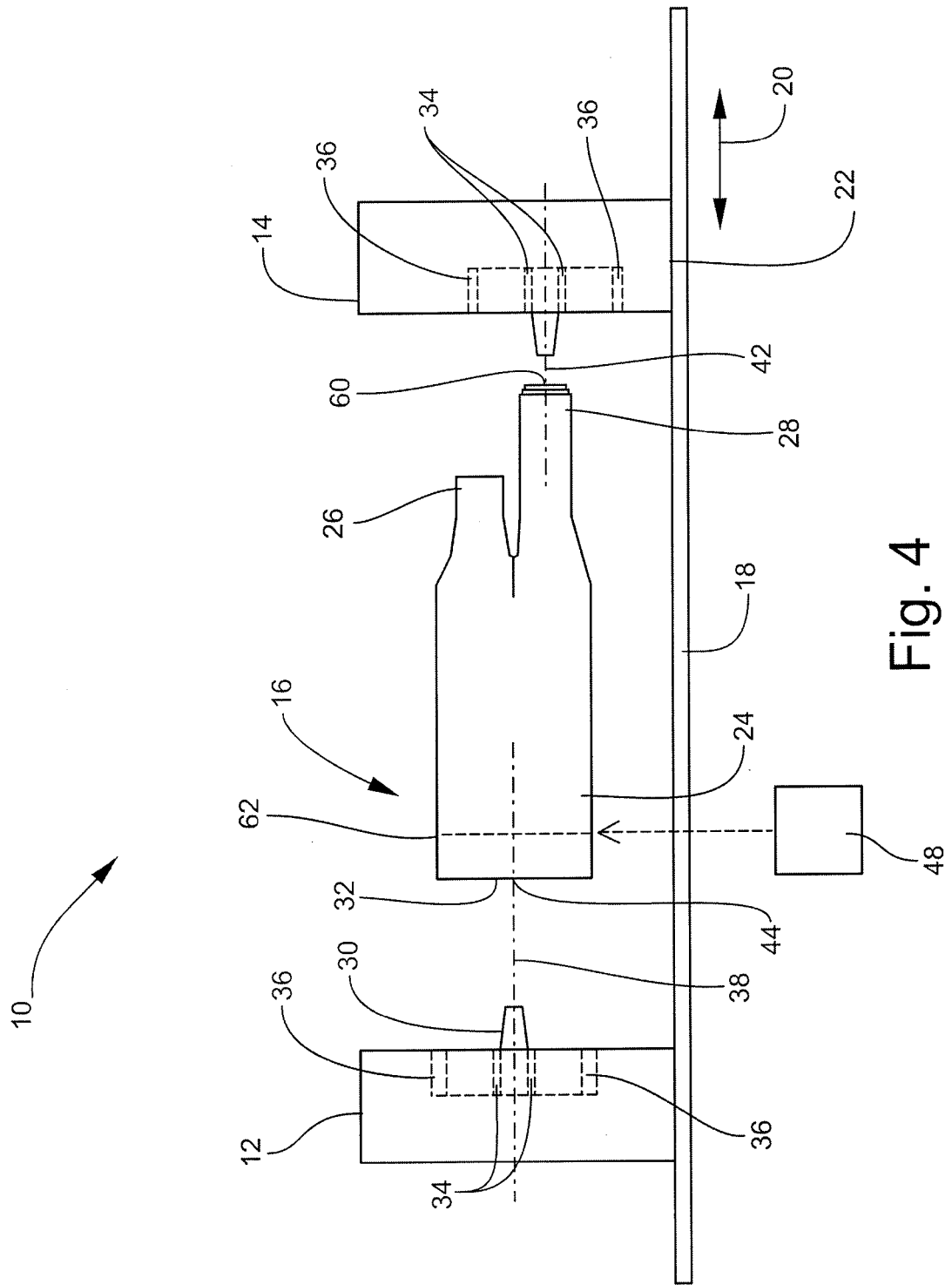
FIG. 4 is a diagrammatic side view of the fabric cutting system shown in FIGS. 1-3, in which the positions of the mandrel body and legs are reversed relative to the centered and offset chucks in an embodiment of the present invention.

To make a cut in fabric on the body 24 of the mandrel 16, the mandrel 16 is again removed from the chucks 12, 14. The mandrel 16 can be removed from the chucks 12, 14 by releasing the clamping mechanism 22 securing the offset chuck 14 to the work surface 18, and moving the offset chuck 14 away from the centered chuck 12 along the direction of movement 20 on the work surface 18. In some embodiments of the fabric cutting system 10, once the mandrel 16 is removed from the chucks 12, 14, it can be reversed in position relative to the two chucks 12, 14, and the body 24 of the mandrel 16 aligned and engaged with the centered chuck 12 along the first longitudinal axis 38 through the center of the centered chuck 12 and the center 44 of the mandrel base 32. This alignment is shown in FIG. 4. The end of the mandrel base 32 is inserted into the body groove 36 in the centered chuck 12.

The second leg 28 (now the longer of the two legs 26, 28) is aligned and engaged with the offset chuck 14 along the second longitudinal axis 42 through the center of the offset chuck 14 and the center 60 of the second leg 28. In some embodiments, as in FIGS. 1-6, the end of the second leg 28 is inserted into the leg groove 34 in the offset chuck 14. In other embodiments, as in FIGS. 7-9, the notches 29 in the end of the second leg 28 are slid over and engage the leg pins 37 about the stepped mount third portion 35 in the offset chuck 14. In still other embodiments, the notches 29 in the ends of the second leg 28 are mounted onto an offset chuck having the universal leg engaging member 72 as in FIG. 10, but offset from the center of the chuck.

The offset chuck 14 is then moved toward the centered chuck 12 such that the mandrel 16 is supported on each end by one of the chucks 12, 14 for rotation. When the fabric cutting system 10 assembly is in place for rotating the mandrel 16, the offset chuck 14 is clamped to the work surface 18 with the clamping mechanism 22 to secure the assembly in place for operation.

Then, the fabric mounted onto the mandrel 16 can be cut about the mandrel body 24. The body cut 62 can be located at a predetermined location on the mandrel body 24. The fabric cutting tool 48 can be adjusted to accommodate for the larger diameter of the mandrel body 24 as compared to the diameter of the first and/or second legs 26, 28, respectively. The mandrel 16 can be rotated about the first and second longitudinal axes 38, 42, respectively, in order to complete the cut 62 about the entire circumference of the mandrel body 24.

In some embodiments of the fabric cutting system 10, whichever portion of the mandrel 16 on which fabric is being cut may be placed on the centered chuck 12 so that the fabric cutting tool 48 can be pre-aligned with that portion of the mandrel 16, and moving the cutting tool 48 can be avoided. In this way, the cutting tool 48 does not have to be reset each time the mandrel 16 is repositioned. The cutting tool 48 can be preset to cut to a location along the first longitudinal axis 38 between the center of the centered chuck 12 and the center of the portion of the mandrel 16 on which the fabric is being cut. The distance from the first longitudinal axis 38 to which the cutting tool 48 is set to cut can vary depending on the diameter of the portion of the mandrel 16 on which fabric is being cut.

Figure 11:
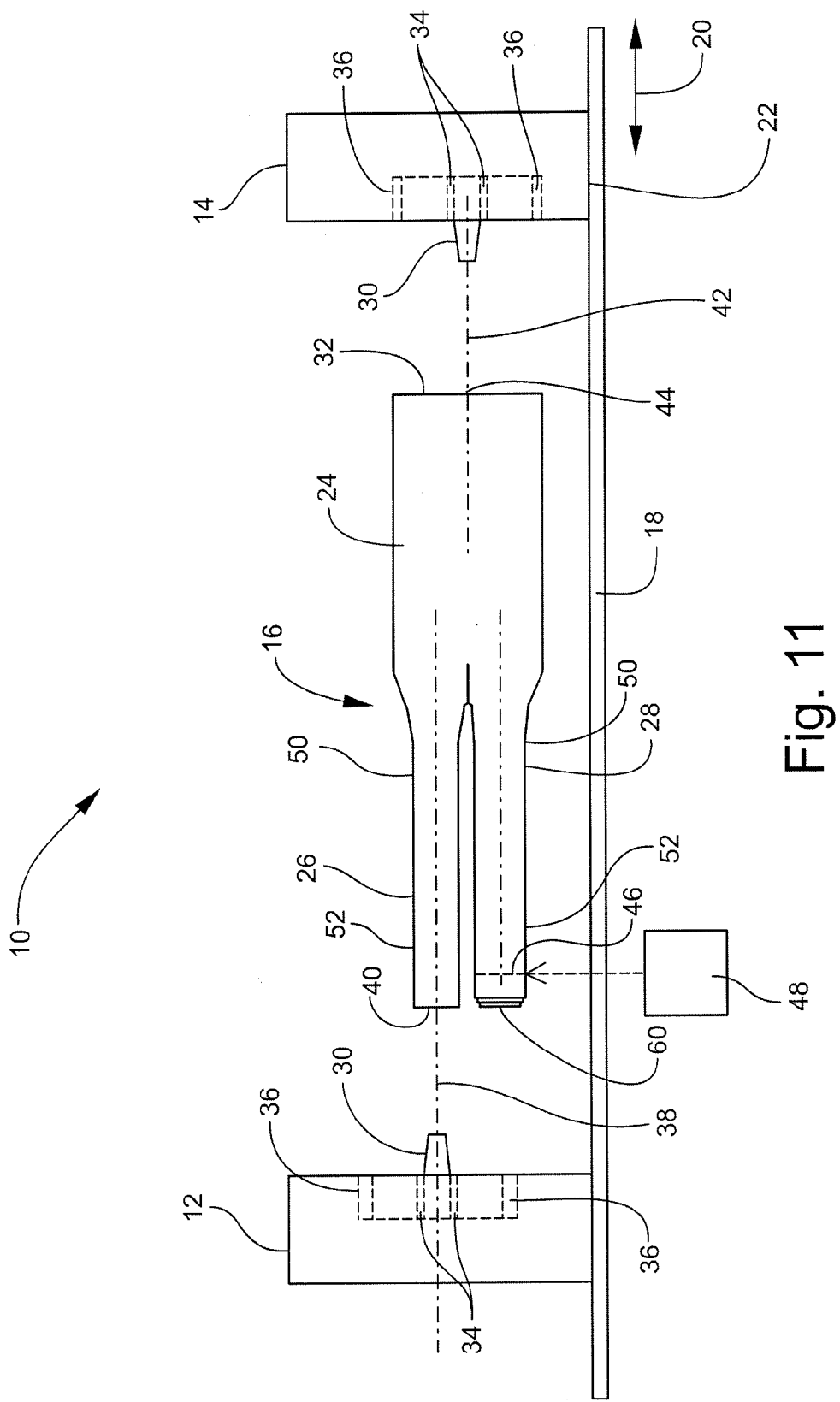
FIG. 11 is a diagrammatic side view of a fabric cutting system comprising a mandrel, a centered chuck, and an offset chuck similar to the embodiment in FIGS. 1-4 and having legs comprising the same length.

Some embodiments of the fabric cutting system 10 can be utilized to cut fabric about the mandrel 16 comprising legs having substantially the same initial length, as shown in the embodiment in FIG. 11. In such an embodiment, each of the legs 26, 28 can include a leg base 50 and a separable leg extension 52. Such an embodiment can be utilized for forming a fabric having a longer leg and a shorter leg.

In the embodiment in FIG. 11, the leg extension 52 can be removed from the leg base 50 on the second leg 28, as shown in FIG. 2. The portion of the fabric leg (not shown) extending beyond the leg base 50 can be turned back onto itself to move that fabric leg out of the way for cutting the fabric on the first leg 26.

The first leg 26 of the mandrel 16 is aligned and engaged with the centered chuck 12 along a first longitudinal axis 38 through the center of the centered chuck 12 and the center 40 of the first leg 26. In some embodiments, as in FIGS. 1-6 and 11, the end of the first leg 26 is inserted into the leg groove 34 in the centered chuck 12. In other embodiments in which the mandrel 16 comprises legs 26, 28 having approximately the same initial length, each leg 26, 28 can comprise the notches 29 in the ends of the legs 26, 28, as in FIGS. 7-9. The notches 29 in the end of the first leg 26 can be slid over and engage the leg pins 37 about the stepped mount third portion 35. In still other embodiments in which the mandrel 16 comprises legs 26, 28 having approximately the same initial length, the notches 29 in the end of the first leg 26 can be mounted onto and engage the universal leg engaging member 72, as in FIGS. 10A and 10B. The base 32 of the mandrel 16 is aligned and engaged with the offset chuck 14 along a second longitudinal axis 42 through the center of the offset chuck and the center 44 of the base 32 of the mandrel body 24. The end of the mandrel base 32 is inserted into the body groove 36 in the offset chuck 14. In other embodiments, the end of the mandrel base 32 can include a pair of opposed notches 29, as shown in FIG. 7, such that one of the notches 29 slides over and engages the base pin 39 in the body groove 36. When the mandrel base 32 is inserted into the body groove 36 and/or one of the notches 29 in the mandrel base 32 engages the base pin 39, the mandrel 16 can be rotated with the chuck 12, 14. The offset chuck 14 is then moved toward the centered chuck 12 such that the mandrel 16 is supported on each end by one of the chucks 12, 14 for rotation. The offset chuck 14 is then clamped to the work surface 18 with the clamping mechanism 22 to secure the assembly in place for operation.

Then, a fabric mounted onto the mandrel 16 can be cut about the first leg 26. The first leg cut 46 can be located on the first leg 26 beyond the end of the leg base 50 of the second leg 28 toward the centered chuck 12. The mandrel 16 can be rotated about the first and second longitudinal axes 38, 42, respectively, in order to complete the cut 46 about the entire circumference of the first leg 26 without interference from the second leg 28 between the fabric cutting tool 48 and the first leg 26.

To make a cut in fabric on the second leg 28, the mandrel 16 is first removed from the chucks 12, 14. The clamping mechanism 22 securing the offset chuck 14 to the work surface 18 can be released, and the offset chuck 14 moved away from the centered chuck 12 along the direction of movement 20 on the work surface 18. When the two chucks 12, 14 are thusly separated, the mandrel 16 can be removed from the chucks 12, 14.

The leg extension 52 can then be reconnected to the leg base 50 on the second leg 28, and the fabric folded onto itself on the leg base 50 of the second leg 28 can be extended back onto the leg extension 52. Next, the leg extension 52 can be removed from the leg base 50 of the first leg 26, as shown in FIG. 2, and the portion of the fabric leg (not shown) extending beyond the leg base 50 can be turned back onto itself to move that fabric leg out of the way for cutting the fabric on the second leg 28.

Once the mandrel 16 is removed from the chucks 12, 14 and the leg extension 52 is removed from the leg base 50 of the first leg 26, the second leg 28 (which is now the longer of the two legs 26, 28) can be aligned and engaged with the centered chuck 12 along the first longitudinal axis 38 through the center of the centered chuck 12 and the center 60 of the second leg 28. The end of the second leg 28 can be inserted into the leg groove 34 in the centered chuck 12, as in the embodiment in FIGS. 1-6. In other embodiments in which each leg 26, 28 comprises the notches 29 in the ends of the legs 26, 28 (as in FIGS. 7-9), the notches 29 in the end of the second leg 28 can be slid over and engage the leg pins 37 about the stepped mount third portion 35. In still other embodiments, the notches 29 in the end of the second leg 28 can be mounted onto and engage the universal leg engaging member 72, as in FIGS. 10A and 10B.

As the second leg 28 is aligned and engaged with the centered chuck 12, the base 32 of the mandrel 16 is aligned and engaged with the offset chuck 14 along the second longitudinal axis 42 through the center of the offset chuck 14 and the center 44 of the base 32 of the mandrel body 24. The end of the mandrel base 32 is inserted into the body groove 36 in the offset chuck 14. In other embodiments in which the end of the mandrel base 32 includes a pair of opposed notches 29 (as shown in FIG. 7), one of the notches 29 can be slid over and engage the base pin 39 in the body groove 36. When the mandrel base 32 is inserted into the body groove 36 and/or one of the notches 29 in the mandrel base 32 engages the base pin 39, the mandrel 16 can be rotated with the chuck 12, 14. The offset chuck 14 is then moved toward the centered chuck 12 such that the mandrel 16 is supported on each end by one of the chucks 12, 14 for rotation. The offset chuck 14 is then clamped to the work surface 18 with the clamping mechanism 22 to secure the assembly in place for operation.

Then, the fabric mounted onto the mandrel 16 can be cut about the second leg 28. The second leg cut 58 can be located on the second leg 28 beyond the end of the leg base 50 of the first leg 26 toward the centered chuck 12. The mandrel 16 can be rotated about the first and second longitudinal axes 38, 42, respectively, in order to complete the cut 58 about the entire circumference of the second leg 28 without interference from the first leg 26 between the fabric cutting tool 48 and the second leg 28.

To make a cut in fabric on the body 24 of the mandrel 16, the mandrel 16 is again removed from the chucks 12, 14. In some embodiments of the fabric cutting system 10, once the mandrel 16 is removed from the chucks 12, 14, it can be reversed in position relative to the two chucks 12, 14, and the body 24 of the mandrel 16 aligned and engaged with the centered chuck 12 along the first longitudinal axis 38 through the center of the centered chuck 12 and the center 44 of the mandrel base 32. This alignment is shown in FIG. 4. The end of the mandrel base 32 can be inserted into the body groove 36 in the centered chuck 12. In other embodiments in which the end of the mandrel base 32 includes a pair of opposed notches 29 (as shown in FIG. 7), one of the notches 29 can be slid over and engage the base pin 39 in the body groove 36.

The second leg 28 (now the longer of the two legs 26, 28) is aligned and engaged with the offset chuck 14 along the second longitudinal axis 42 through the center of the offset chuck 14 and the center 60 of the second leg 28. In some embodiments, as in FIGS. 1-6, the end of the second leg 28 is inserted into the leg groove 34 in the offset chuck 14. In other embodiments, as in FIGS. 7-9, the notches 29 in the end of the second leg 28 are slid over and engage the leg pins 37 about the stepped mount third portion 35 in the offset chuck 14. In still other embodiments, the notches 29 in the ends of the second leg 28 are mounted onto an offset chuck having the universal leg engaging member 72 as in FIG. 10, but offset from the center of the chuck.

The offset chuck 14 is then moved toward the centered chuck 12 such that the mandrel 16 is supported on each end by one of the chucks 12, 14 for rotation, and the offset chuck 14 is clamped to the work surface 18 with the clamping mechanism 22 to secure the assembly in place for operation. The mandrel 16 can then be rotated about the first and second longitudinal axes 38, 42, respectively, in order to complete the cut 62 of the fabric about the entire circumference of the mandrel body 24.

As shown in FIGS. 1-11, in some embodiments of the fabric cutting system 10, each of the chucks 12, 13, 14 can have the same size and configuration. That is, each of the centered chucks 12, 13 and offset chucks 14 can have the same size and configuration of tapered mount 30, stepped mount portions 31, 33, 35, or universal leg engaging member 72, leg groove 34, and body groove 36 such that both the legs 26, 28 of the mandrel 16 and the body 24 of the mandrel 16 can fit into and be supported by either chuck 12 or 13 and 14 for rotation. This consistency between chucks 12 or 13 and 14 allows interchangeability of the ends of the mandrel 16 with either chuck 12 or 13 and 14 so that the mandrel 16 can be repositioned without having to adjust the location of the fabric cutting tool 48 between the chucks 12 or 13 and 14.

In some embodiments of the fabric cutting system 10, the mandrel 16, which is a cutting mandrel, can also be used for heat-setting fabric on the mandrel 16. Using the mandrel 16 for both cutting and heat-setting avoids having to remove the fabric from one mandrel 16 and place it on another mandrel. This avoids the risk of the fabric wrinkling and the possible difficulty of placing the fabric in the proper position on the heat-setting mandrel.

In another aspect of the fabric cutting system 10, the fabric cutting tool 48, or device, can comprise a cutting laser. Preferably, the cutting laser is programmable so that focal distances between the laser lens and the mandrel 16 can be easily and/or automatically adjusted to preset distances for quality cutting of different diameters on the mandrel 16. For example, fabric mounted on a plurality of mandrel legs 26, 28 can be cut adjacent the centered chuck 12, 13 by the cutting laser having a cutting focal distance preset for the diameter of the legs 26, 28. When the mandrel 16 is reversed in position between the two chucks 12 or 13 and 14, fabric mounted on the mandrel body 24 can be cut adjacent the centered chuck 12 by the cutting laser having a different cutting focal distance preset for the diameter of the mandrel body 24. Having an optimal cutting focal distance from the laser to the fabric avoids insufficient cutting when the laser is too far from the fabric and burning the fabric when the laser is too close to the fabric.

In some embodiments, the cutting laser can be a multi-axis laser. A multi-axis laser comprises multiple power heads from which different laser beams can be emitted. A cutting laser beam emitted from each power head can be focused to a different focal point. Accordingly, fabric on the mandrel legs 26, 28 can be cut by a first power head having a preset focal point, or distance, for the mandrel legs 26, 28, and fabric on the larger diameter mandrel body 24 can be cut by a second power head having a preset focal point, or distance, for the mandrel body 24. In some embodiments of the fabric cutting system 10, fabric on the larger diameter mandrel body 24 can be cut by a second power head of a multi-axis laser after the mandrel body 24 is removed from the offset chuck 14 and placed onto the centered chuck 12 or 13. This allows elimination of the step of adjusting a single focus laser to a desired cutting focal point for the larger diameter mandrel body 24. In other embodiments, the fabric on the larger diameter mandrel body 24 can be cut by a second power head of a multi-axis laser while the mandrel body 24 is still secured in the offset chuck 14. This allows elimination of the step of removing the mandrel 16 from the chucks 12 or 13 and 14 and placing the mandrel body 24 in the centered chuck 12.

In some embodiments, the cutting laser can utilize between about 30 and about 35 watts of power to accomplish a cut of fabric. Lasers having power output in this range are sometimes referred to as "engraving" lasers. Often, cutting lasers utilize greater than 50 watts of power to accomplish a cut. However, an engraving-type laser utilizing between about 30 and about 35 watts to cut a fabric can provide cuts having a straighter edge and a better seal of the fabric edge than fabrics cut with lasers utilizing greater than 50 watts. The quality of laser cuts for fabric useful in medical applications can be enhanced by optimizing the combination of power, speed, and density (wattage per square unit) of the laser. The optimal combination of these variables can vary depending on the type of fabric or material being cut.

Some embodiments of the present invention can include a method of cutting a fabric utilizing embodiments of the fabric cutting system 10 described herein. For example, one illustrative method of cutting fabric can comprise mounting a tubular fabric having a plurality of fabric legs onto the mandrel 16 comprising the body 24, the first leg 26, and the second leg 28 shorter than the first leg 26. The first leg 26 is inserted into the center of the centered chuck 12 or 13, and the mandrel body 24 is inserted into the offset chuck 14 at a point offset from the center of the offset chuck 14. The mandrel 16 can then be rotated between the chucks 12 or 13 and 14, and the entire circumference of the fabric about the first leg 26 can be cut at a location beyond the end of the second leg 28. In this way, the first leg cut 46 can be accomplished by the fabric cutting tool 48 having a line of contact with the first leg cut 46 location unimpeded by the second leg 28.

In some embodiments, the first leg 26 can comprise the leg extension 52 removably attached to the leg base 50, and the method can further comprise removing the mandrel 16 from the centered chuck 12 or 13 and the offset chuck 14, removing the leg extension 52 from the leg base 50, and folding a portion of the fabric leg extending beyond the leg base 50 back onto itself on the leg base 50. The second leg 28 is inserted into the center of the centered chuck 12 or 13, and the mandrel body 24 is inserted into the offset chuck 14 at the point offset from the center of the offset chuck 14. The mandrel 16 can then be rotated between the chucks 12 or 13 and 14, and the entire circumference of the fabric about the second leg cut 58 at a location beyond the end of the leg base 50 of the first leg 28. That is, the second leg cut 58 can be accomplished by the fabric cutting tool 48 having a line of contact with the second leg cut 58 location unimpeded by the first leg 26.

In some embodiments, such a method can further comprise removing the mandrel 16 from the centered chuck 12 or 13 and the offset chuck 14, inserting the mandrel body 24 into the center of the centered chuck 12 or 13, and inserting the second leg 28 into the offset chuck 14 at the point offset from the center of the offset chuck 14. The mandrel 16 can then be rotated between the chucks 12, 13, 14, and the entire circumference of the fabric cut about the mandrel body 24. Preferably, the fabric about the first leg 26 and the second leg 28 is cut before cutting the fabric about the mandrel body 24. In this way, the full length of the fabric on the mandrel body 24 is in place to help grip the mandrel body 24 and stabilize the fabric while being cut on the legs, 26, 28 resulting in more accurate first and second leg cuts, 46, 58, respectively. In certain embodiments, the cut fabric comprises a vascular graft.

In some embodiments of such a method, the centered chuck 12, 13 can be fixedly attached to the work surface 18 and configured to receive either one of the mandrel legs 26, 28 or body 24 to rotatingly support the mandrel 16 in the center of the centered chuck 12. And, the offset chuck 14 can be spaced apart from and opposed to the centered chuck 12, 13, movably attached to the work surface 18, and configured to receive either one of the mandrel legs 26, 28 or body 24 to rotatingly support the mandrel 16 at the point offset from the center of the offset chuck 14. In certain embodiments, the method can further comprise heat-setting the fabric on the mandrel 16.

In some embodiments of such a method, the fabric can be cut utilizing a cutting laser. The cutting laser may be programmable with different focal distances for cutting different diameters on the mandrel. In certain embodiments, the cutting laser can be a multi-axis laser adapted to emit laser beams to different focal cutting points. In other embodiments, the laser can be capable of emitting a laser beam having between about 30 and about 35 watts of power to cut the fabric.

In some embodiments of such a method, the fabric cutting system 10 can comprise the mandrel 16 comprising legs having substantially the same initial length, as shown in and described relative to the embodiment in FIG. 11.

Embodiments of the fabric cutting system 10 and method as described herein can be utilized in medical applications, including, for example, in producing vascular and endovascular implants such as stents, stent-grafts, and heart valves. Some products made by the fabric cutting system 10 and/or method may be applicable for use in various other types of anatomical structures and locations, for example, in shunts between organs and/or in gastrointestinal, pulmonary, neurological, and/or other structures and locations of a human or animal body.

Figure 12:
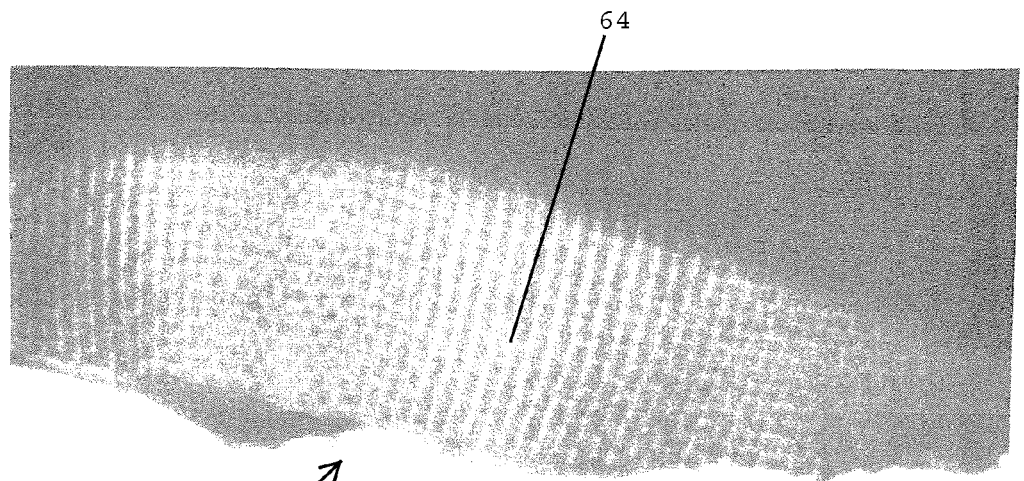
FIG. 12 is a view of a microscopic photographic view of the edge of a tubular fabric manually cut with a soldering iron-type tool in a conventional cutting process.
Figure 13:
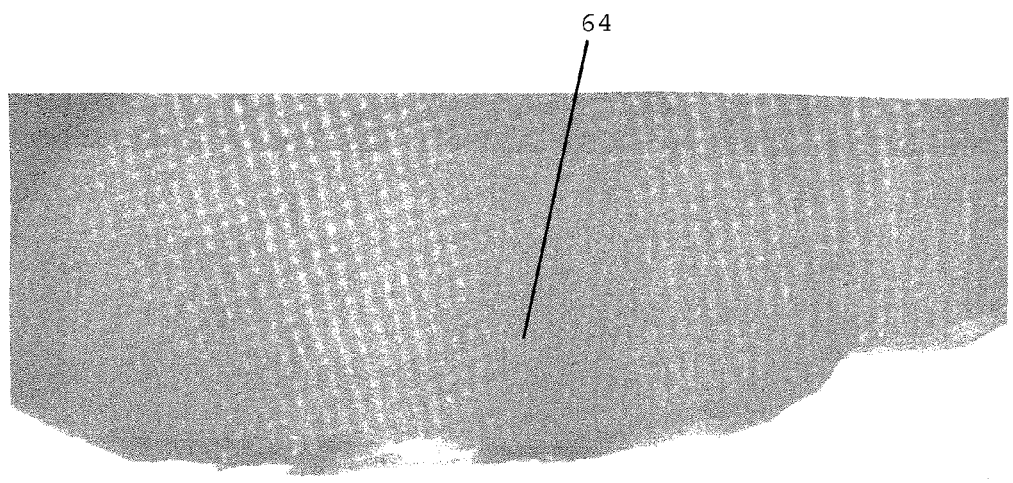
FIG. 13 is a view of a microscopic photographic view of the edge of another tubular fabric manually cut with a soldering iron-type tool in a conventional cutting process.
Figure 14:
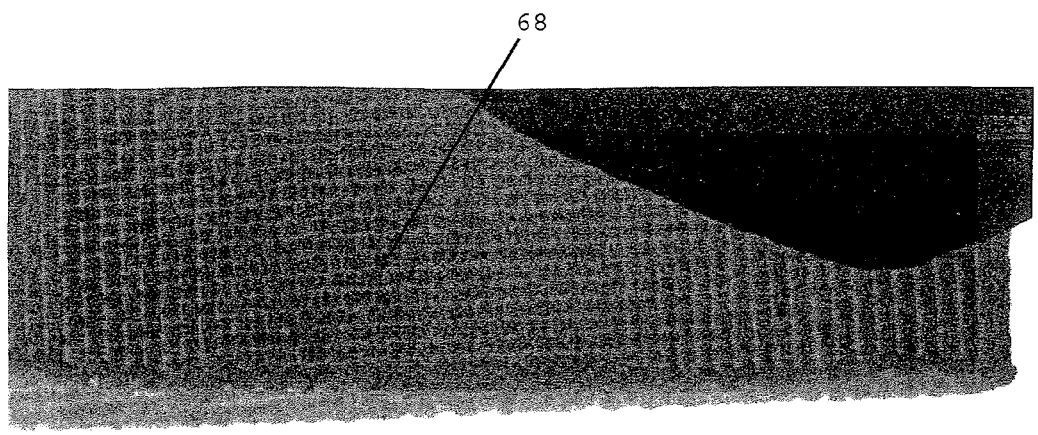
FIG. 14 is a microscopic photographic view of the edge a long leg of a tubular fabric cut with a laser in accordance with an embodiment of the present invention.
Figure 15:
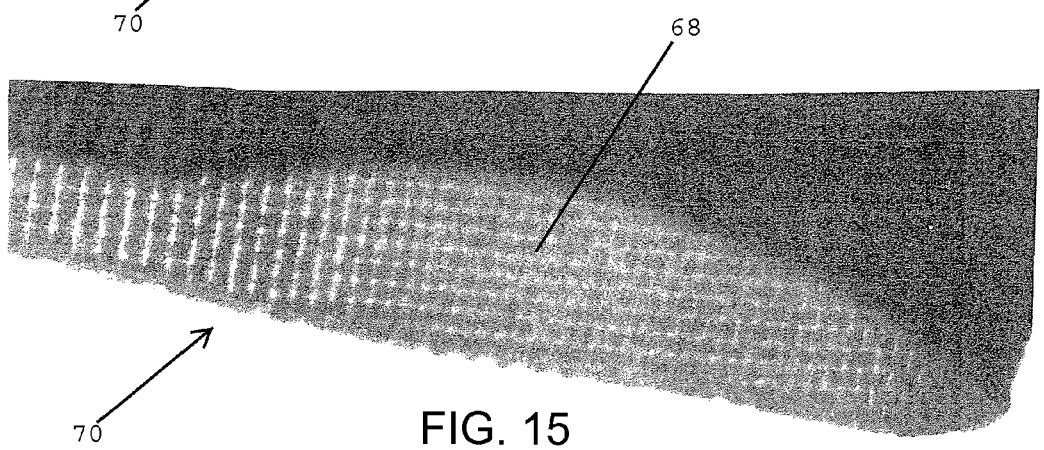
FIG. 15 is a microscopic photographic view of the edge a short leg of a tubular fabric cut with a laser in accordance with an embodiment of the present invention.
Figure 16:
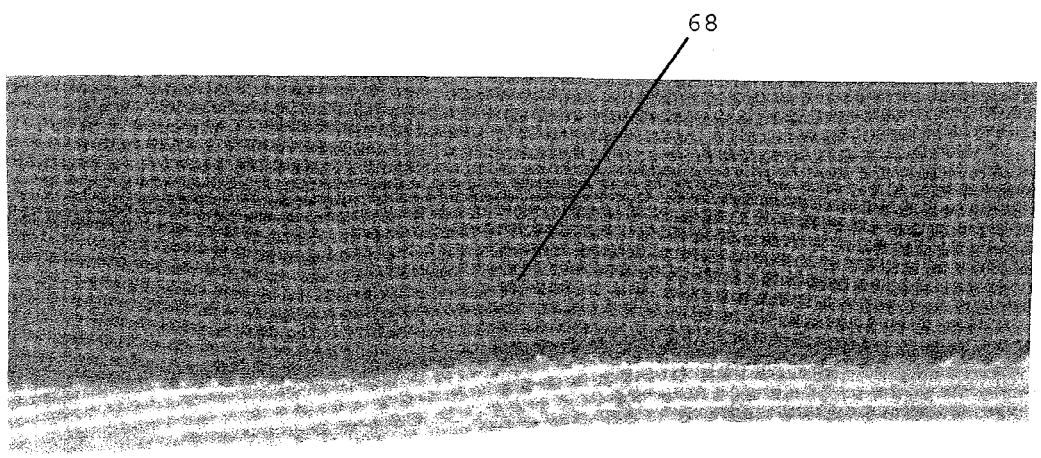
FIG. 16 is a microscopic photographic view of the edge the body of a tubular fabric cut with a laser in accordance with an embodiment of the present invention.

The fabric cutting system 10 and/or method of the present invention provide(s) numerous advantages over conventional fabric cutting systems and methods. For example, the present invention advantageously provides the fabric cutting system 10 and method that provide reliably precise cuts. FIGS. 12 and 13 are microscopic views of the edges 66 of tubular fabrics 64 manually cut using a soldering iron according to a conventional cutting technique, and illustrate that the edge 66 of a fabric 64 cut in this manner can be uneven and can include loose fibers. In contrast, FIGS. 14-16 are microscopic photographic views of the edges 70 of the first leg 26, the second leg 28, and the body 24, respectively, of a tubular fabric 68 cut with a laser in accordance with an embodiment of the present invention. The fabric edges 70 shown in FIGS. 14-16 are evenly cut and are completely sealed. Accordingly, the fabric cutting system 10 and method of the present invention can provide cut tubular fabrics 68 that meet quality control requirements for use in medical applications.

Another advantage is that the present invention can provide the fabric cutting system 10 and method that provide a direct and unimpeded line of contact between the fabric cutting tool 48 and multiple legs 26, 28 on the mandrel 16.

Another advantage is that the present invention can provide the fabric cutting system 10 and method in which positions of the mandrel 16 are interchangeable so that the fabric cutting tool 48 can remain in alignment with a preset location relative to the longitudinal axis 38.

Another advantage is that the present invention can provide the cutting mandrel 16 that can also be used as a heat-setting mandrel. Using the mandrel 16 for both cutting and heat-setting avoids having to remove the fabric from one mandrel 16 and place it on another mandrel, thereby avoiding the risk of the fabric wrinkling and the possible difficulty of placing the fabric in the proper position on a heat-setting mandrel.

Another advantage is that the fabric on the legs 26, 28 of the mandrel 16 can be cut first, before cutting fabric on the mandrel body 24, which allows the fabric on the mandrel body 24 to better grip the mandrel body 24 to help keep the fabric in place while the fabric on the legs 26, 28 is being cut, resulting in more accurate first and second leg cuts.

Another advantage is that the present invention can provide the fabric cutting system 10 and method comprising a laser utilizing between about 30 and about 35 watts to cut a fabric, thereby providing a straighter edge and a better seal of the fabric edge 70 than fabrics cut with lasers utilizing higher wattage.

Another advantage is that the present invention can provide the fabric cutting system 10 and method that are efficient and cost-effective. For example, embodiments of the fabric cutting systems 10 and methods according to the present invention can reduce waste of fabric from about 40-50 percent in conventional systems and methods to about 10 percent or less.

Although the present invention has been described with reference to particular embodiments, it should be recognized that these embodiments are merely illustrative of the principles of the present invention. Those of ordinary skill in the art will appreciate that the fabric cutting system and/or method of the present invention may be constructed and implemented in other ways and embodiments. Accordingly, the description herein should not be read as limiting the present invention, as other embodiments also fall within the scope of the present invention.

What is claimed is:

1. A method of cutting a fabric, comprising:
   mounting a tubular fabric having a plurality of fabric legs onto a mandrel comprising a body, a first leg, and a second leg shorter than the first leg, the first leg comprising a leg extension removably attached to a leg base;
   inserting the first leg into a center of a centered chuck;
   inserting the mandrel body into an offset chuck at a point offset from a center of the offset chuck;
   rotating the mandrel between the chucks;
   cutting the entire circumference of the fabric about the first leg at a location beyond the end of the second leg;

removing the mandrel from the centered and offset chucks;
removing the leg extension from the leg base;
folding a portion of the fabric leg extending beyond the leg base back onto itself on the leg base;
inserting the second leg into the center of the centered chuck;
inserting the mandrel body into the offset chuck at the point offset from the center of the offset chuck;
rotating the mandrel between the chucks; and
cutting the entire circumference of the fabric about the second leg at a location beyond the end of the leg base of the first leg.

2. A method of cutting a fabric, comprising:
mounting a tubular fabric having a plurality of fabric legs onto a mandrel comprising a body, a first leg, and a second leg shorter than the first leg, the first leg comprising a leg extension removably attached to a leg base;
inserting the first leg into a center of a centered chuck;
inserting the mandrel body into an offset chuck at a point offset from a center of the offset chuck;
rotating the mandrel between the chucks;
cutting the entire circumference of the fabric about the first leg at a location beyond the end of the second leg;
removing the mandrel from the centered and offset chucks;
removing the leg extension from the leg base;
folding a portion of the fabric leg extending beyond the leg base back onto itself on the leg base;
inserting the second leg into the center of the centered chuck;
inserting the mandrel body into the offset chuck at the point offset from the center of the offset chuck;
rotating the mandrel between the chucks;
cutting the entire circumference of the fabric about the second leg at a location beyond the end of the leg base of the first leg;
removing the mandrel from the centered and offset chucks;
inserting the mandrel body into the center of the centered chuck;
inserting the second leg into the offset chuck at the point offset from the center of the offset chuck;
rotating the mandrel between the chucks; and
cutting the entire circumference of the fabric about the mandrel body.

3. A method of cutting a fabric comprising:
mounting a tubular fabric having a plurality of fabric legs onto a mandrel comprising a body, a first leg, and a second leg shorter than the first leg, the first leg comprising a leg extension removably attached to a leg base;
inserting the first leg into a center of a centered chuck;
inserting the mandrel body into an offset chuck at a point offset from a center of the offset chuck;
rotating the mandrel between the chucks;
cutting the entire circumference of the fabric about the first leg at a location beyond the end of the second leg;
removing the mandrel from the centered and offset chucks;
removing the leg extension from the leg base;
folding a portion of the fabric leg extending beyond the leg base back onto itself on the leg base;
inserting the second leg into the center of the centered chuck;
inserting the mandrel body into the offset chuck at the point offset from the center of the offset chuck;
rotating the mandrel between the chucks;
cutting the entire circumference of the fabric about the second leg at a location beyond the end of the leg base of the first leg;
removing the mandrel from the centered and offset chucks;
inserting the mandrel body into the center of the centered chuck;
inserting the second leg into the offset chuck at the point offset from the center of the offset chuck;
rotating the mandrel between the chucks; and
cutting the entire circumference of the fabric about the mandrel body;
wherein the fabric about the first leg and the second leg is cut before cutting the fabric about the mandrel body.

4. The method of claim 1,
wherein the centered chuck is fixedly attached to a work surface and configured to receive either one of the mandrel legs or body to rotatingly support the mandrel in the center of the centered chuck; and
wherein the offset chuck is spaced apart from and opposed to the centered chuck, movably attached to the work surface, and configured to receive either one of the mandrel legs or body to rotatingly support the mandrel at the point offset from the center of the offset chuck.

5. The method of claim 1, further comprising heat-setting the fabric on the mandrel.

6. The method of claim 1, wherein cutting the fabric further comprises cutting the fabric with a cutting laser.

7. The method of claim 6, further comprising programming the cutting laser with different focal distances for cutting different diameters on the mandrel.

8. The method of claim 6, wherein cutting the fabric further comprises cutting the fabric with a multi-axis laser having a plurality of power heads, each power head adapted to emit a laser beam to a different focal cutting point.

9. The method of claim 6, further comprising emitting a laser beam having between about 30 and about 35 watts of power to cut the fabric.

10. The method of claim 1, wherein the cut fabric comprises a vascular graft.

* * * * *